(12) United States Patent
Geebelen

(10) Patent No.: US 9,785,747 B2
(45) Date of Patent: Oct. 10, 2017

(54) METHOD FOR DESIGNING A SURGICAL GUIDE

(71) Applicant: MATERIALISE N.V., Leuven (BE)

(72) Inventor: Benjamin Geebelen, Haasrode (BE)

(73) Assignee: Materialise NV, Leuven (BE)

( * ) Notice: Subject to any disclaimer, the term of this patent is extended or adjusted under 35 U.S.C. 154(b) by 69 days.

(21) Appl. No.: 14/742,391

(22) Filed: Jun. 17, 2015

(65) Prior Publication Data
US 2015/0282886 A1 Oct. 8, 2015

Related U.S. Application Data

(63) Continuation of application No. PCT/EP2013/076889, filed on Dec. 17, 2013.

(60) Provisional application No. 61/737,871, filed on Dec. 17, 2012.

(51) Int. Cl.
*A61B 17/17* (2006.01)
*A61B 17/15* (2006.01)
*G06F 19/00* (2011.01)
*A61B 34/10* (2016.01)

(52) U.S. Cl.
CPC .......... *G06F 19/3437* (2013.01); *A61B 17/15* (2013.01); *A61B 17/17* (2013.01); *A61B 17/1757* (2013.01); *A61B 34/10* (2016.02); *A61B 17/1782* (2016.11); *A61B 2034/108* (2016.02)

(58) Field of Classification Search
CPC .......................................... A61B 17/15–17/158
See application file for complete search history.

(56) References Cited

U.S. PATENT DOCUMENTS

| | | | | |
|---|---|---|---|---|
| 8,579,911 B2* | 11/2013 | Dudasik | ............ | A61B 17/1757 606/86 A |
| 2005/0234466 A1* | 10/2005 | Stallings | ............... | A61B 17/15 606/88 |
| 2009/0209884 A1* | 8/2009 | Van Vorhis | ............... | A61F 2/38 600/595 |
| 2009/0222014 A1* | 9/2009 | Bojarski | ............ | A61B 17/155 606/88 |
| 2011/0319745 A1* | 12/2011 | Frey | ....................... | A61B 17/15 600/407 |

FOREIGN PATENT DOCUMENTS

| | | | | |
|---|---|---|---|---|
| CH | WO 2012156466 A1 * | 11/2012 | ............ | A61B 17/15 |
| WO | 2012156466 A1 | 11/2012 | | |

OTHER PUBLICATIONS

International Search Report and Written Opinion issued May 6, 2014 on related application PCT/EP2013/076889 filed Dec. 17, 2013.

* cited by examiner

*Primary Examiner* — Zade Coley

(57) ABSTRACT

Provided herein is a method for generating and manufacturing a surgical guide for guiding a surgical intervention on a bone of a patient, and surgical guides obtainable by said method. The guides provided herein comprise an anatomy engagement surface or contact points for contacting with the first bone, and further comprise a support surface configured for contacting a second bone of the patient, over a certain range of motion of said second bone.

12 Claims, 3 Drawing Sheets

A

B

METHOD FOR DESIGNING A SURGICAL GUIDE

CROSS-REFERENCE TO RELATED APPLICATIONS

This application is a continuation under 35 U.S.C. §120 of International Application No. PCT/EP2013/076889, filed Dec. 17, 2013 (and published on Jun. 26, 2014 in the English language as International Publication No. WO 2014/095853), which claims priority to U.S. Provisional Application No. 61/737,871, filed Dec. 17, 2012. Each of the above-referenced patent applications is hereby incorporated by reference in its entirety.

BACKGROUND OF THE INVENTION

Field of the Invention

Provided herein is a method for generating and manufacturing a surgical guide for guiding a surgical intervention on a bone, and surgical guides obtainable by said method.

Description of the Related Technology

For a number of years, the combination of virtual pre-operative planning and patient-specific surgical instruments has been available for performing complex orthopedic surgeries. This combination allows the surgeon to meticulously plan the surgery in advance on a virtual 3D model, and then execute this planning in the operating room by using patient-specific surgical instruments, which are unique to the patient and the planned surgery. The patient-specific instruments typically comprise an anatomy engagement surface which matches a part of the patient anatomy, and may guide the surgeon in performing operations such as drilling, osteotomies, and placing pins and screws.

However, for small bones or bones without pronounced features such as vertebrae, it is difficult to create patient-specific instruments providing a unique fit on the bone, wherein the fit is sufficiently stable. Although the stability of the fit may be increased by extending the support surface across a joint to an adjacent bone, this is often not a very reliable solution. Indeed, this approach requires bringing both bones of the joint to the exact same relative position that they were in when the medical images were taken on which the design of the patient-specific instrument is based. Once this relative position is obtained, the bones must further be held in this position at least until the instrument has been secured to the bone. More often than not this is very hard to accomplish in practice. Accordingly, there is a need of improved surgical guides mitigating at least part of the problems described above.

SUMMARY

Described herein are methods for generating a surgical guide for guiding a surgical intervention on a bone, and surgical guides obtainable by said method. More particularly, provided herein are methods for generating a surgical guide for guiding a surgical intervention on a first bone of a patient, comprising the steps of:
(a) providing a three-dimensional (3D) model of at least a part of said first bone and of a second bone of said patient;
(b) determining or identifying a contact surface on said first bone;
(c) identifying a contact surface on said second bone;
(d) determining a range of motion of said second bone relative to said first bone in at least one degree of freedom;
(e) generating a surgical guide, said guide comprising:
  (1) one or more anatomy engagement surfaces or anatomy contact points corresponding to at least a part of said contact surface on said first bone;
  (2) a support surface configured for contacting at least a part of said contact surface on said second bone over the entire range of motion of said second bone as determined in step (d);
  (3) a bridge element connecting said anatomy engagement surface or anatomy contact points and said support surface; and
  (4) a functional feature for assisting said surgical intervention.

In particular embodiments, step (d) comprises determining an outer hull corresponding to a range of motion relative to said first bone of said contact surface on said second bone, and the surgical guide is generated such that said support surface matches said outer hull.

In certain embodiments, said second bone is a bone adjacent to said first bone. In certain embodiments, said first bone and said second bone are two adjacent vertebrae. In particular embodiments, said first bone and said second bone are adjacent phalanx bones. In particular embodiments, step (d) comprises determining a range of motion of said second bone relative to said first bone in at least two degrees of freedom.

In certain embodiments, the method described herein further comprises the step of manufacturing said surgical guide via additive manufacturing.

In certain embodiments, the functional feature is a guiding feature, more particularly a dedicated guiding feature, such as those selected from the list consisting of a drill guide, a screw hole, and a cutting slot.

In particular embodiments, the surgical guide further comprises one or more fixation features.

In certain embodiments, the surgical guide is designed as a single piece. In other embodiments, the surgical guide is designed as two or more connectable parts.

Further provided herein is a surgical guide obtainable by the method described herein. Further provided herein is a computer program configured for carrying out the methods described herein. The independent and dependent claims set out particular embodiments envisaged herein. Features from the dependent claims may be combined with features of the independent or other dependent claims as appropriate.

In particular embodiments, the surgical guides obtained by the methods described herein may provide for a stable and unique fit onto a bone, even on bones providing a relatively small contact surface and/or a contact surface without pronounced features. More particularly, the surgical guides may allow for increasing the support surfaces of surgical instruments, without forcing the medical staff to spend a lot of energy in precisely reconstructing the patient's position according to a medical image. Indeed, the surgical guides may allow for contacting two bones of a patient, for example adjacent bones at a joint, even when the relative position of the bones during surgery is different from the relative position the bones were in when medical images were taken for planning the surgery.

The above and other characteristics, features and advantages of the present methods will become apparent from the following detailed description, which illustrates, by way of example, the principles of the disclosed methods.

BRIEF DESCRIPTION OF THE DRAWINGS

The following description of the figures of specific embodiments of the methods and instruments described herein is merely exemplary in nature and is not intended to limit the present teachings, their application or uses. Throughout the drawings, corresponding reference numerals indicate like or corresponding parts and features.

B: A surgical guide (6) is positioned onto two vertebrae (1, 2) via two engagement surfaces (8, 9).

Figure 2:
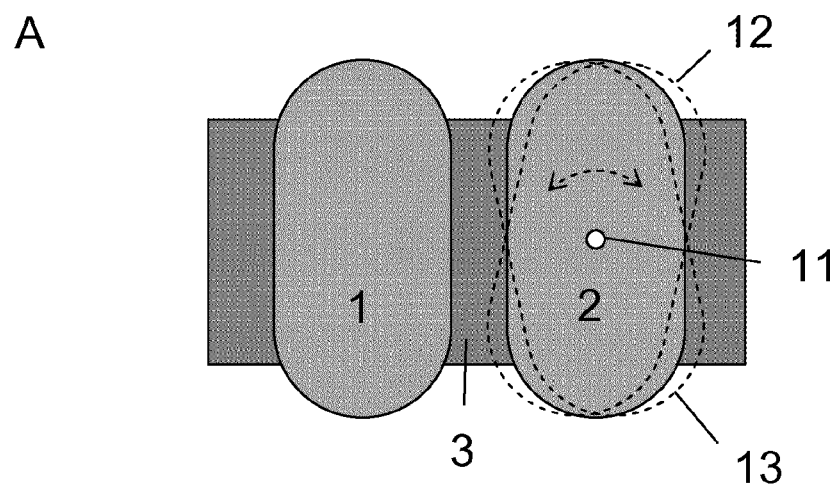
Figure 2:
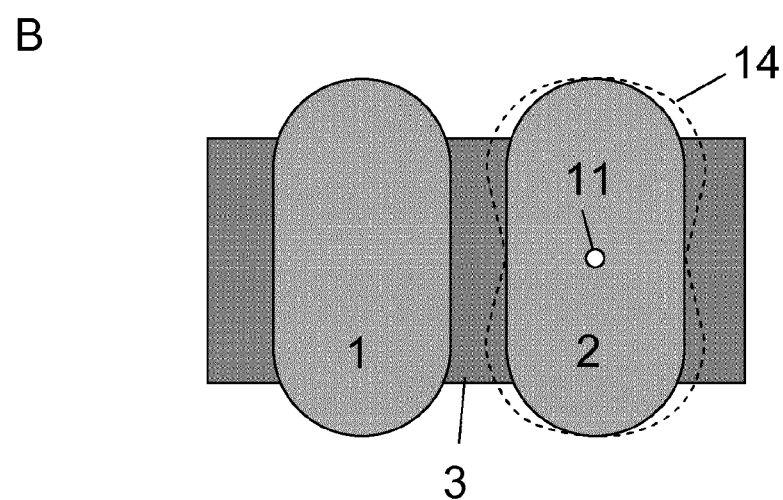

FIG. 2 A, B: schematic illustration of two adjacent vertebrae (1, 2) showing the contour of a vertebra (2) during extreme flexion (12) and extreme extension (13). The contours can be considered forming an outer hull (14).

Figure 3:
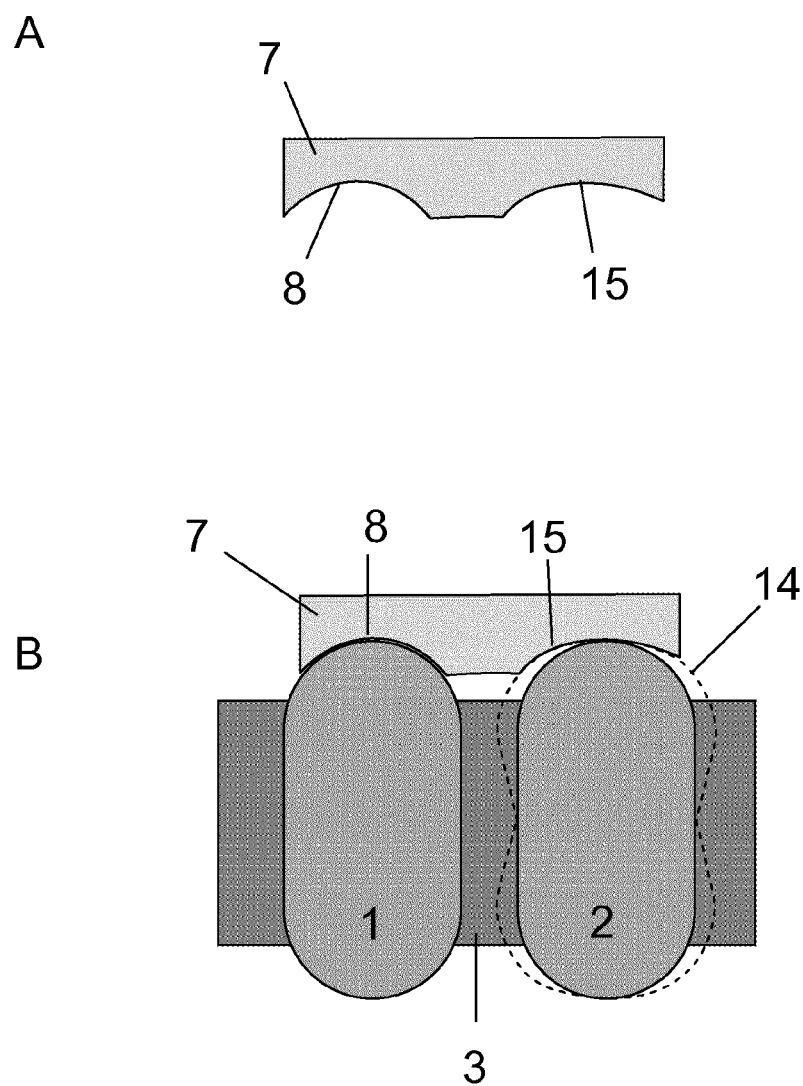

FIG. 3 A, B: schematic illustration of a surgical guide (7) obtainable according to a particular embodiment of the method described herein, as such (A) and when positioned onto adjacent vertebrae (1, 2) (B). In the figures, the following numbering is used: 1, 2—vertebra; 3, 4—intervertebral disc; 5, 6, 7—guide; 8, 9—engagement surface; 10—extension; 11—axis of rotation; 12—extreme flexion; 13—extreme extension; 14—outer hull; 15—support surface.

DETAILED DESCRIPTION OF CERTAIN INVENTIVE EMBODIMENTS

While potentially serving as a guide for understanding, any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably or less, and still more preferably +/−0.1% or less of and from the specified value, insofar such variations are appropriate to ensure one or more of the technical effects envisaged herein. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure. The terms or definitions used herein are provided solely to aid in the understanding of the teachings provided herein.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

Described herein are methods for generating a surgical guiding instrument, also referred to herein as "guide" or "guiding instrument", for guiding a surgical intervention on a first bone in a human or animal patient. In preferred embodiments, the patient may be a human patient.

More particularly, provided herein is a method for generating a surgical guiding instrument for guiding a surgical intervention on a first bone of a patient, which ensures a contact surface with both the first bone on which the surgical intervention is to take place, and a second bone of said patient. In particular embodiments, the second bone is a bone adjacent to the first bone. In view of the movement of the second bone relative to the first bone, the contact surface of the instrument with the second bone is one which takes into account this movement, i.e. encompasses a series of contact points for various positions of the second bone. Thus the method provided herein encompasses taking into account a range of motion of the second bone relative to the first bone and providing a support surface based thereon. In particular embodiments, a method is provided comprising the steps of:
 (a) providing a three-dimensional (3D) model of at least a part of said first bone, and of a second bone of said patient;
 (b) determining or identifying a contact surface on said first bone;
 (c) determining or identifying a contact surface on said second bone;
 (d) determining a range of motion of said second bone relative to said first bone in at least one degree of freedom; and (e) generating a surgical guide, said guide comprising:
  (1) one or more engagement surfaces or anatomy contact points corresponding to at least a part of said contact surface on said first bone;

(2) a support surface configured for contacting at least a part of said contact surface on said second bone, over the range of motion of said second bone as determined in step (d);

(3) a bridge element connecting said anatomy engagement surface or anatomy contact points and said support surface; and (4) a functional feature for assisting said surgical intervention, will be explained more in detail herein below.

In step (a) of the method described herein, a three-dimensional (3D) model is provided of at least a part of said first bone, and of a second bone of said patient. In certain embodiments, the model is a model of the entire first bone and second bone.

In particular embodiments, the second bone is adjacent to the first bone. More particularly, the first and second bones may be two adjacent bones at a single joint. The term "joint" as used herein refers to the location at which two or more bones make contact. Joints are typically constructed to allow movement and provide mechanical support.

In particular embodiments, the first and second bones are two vertebrae, more particularly two adjacent vertebrae. Adjacent vertebrae are typically joined by an intervertebral disc forming a cartilaginous joint and allow slight relative movement of the vertebrae.

In certain embodiments, the first bone and the second bone are (adjacent) phalanx bones, also known as phalanges. Phalanx bones are the bones forming the toes and the fingers in humans and certain animals such as primates. Interphalangeal joints, i.e. joints between phalanges, typically provide a large lateral stability and only permit flexion and extension movements, i.e. rotational movement in one degree of freedom.

In particular embodiments, the model is provided based on volume information of the first and second bone. Accordingly, in particular embodiments, the methods may further comprise the steps of:

(a1) obtaining volume information of the first and second bone; and (a2) generating a 3D model of said first and second bone, based on the information obtained in step (a1).

In particular embodiments, step (a1) may include the step of taking images of the bones. The images may be any type of image that can be used to create a 3D model of the first and second bone part. In particular embodiments, the images are 2D or 3D images. The images can be taken using any type of imaging apparatus or imaging technique which allows imaging or scanning the bones in an accurate manner. These may include equipment such as cameras and scanners for industrial, household or medical use. In particular embodiments the imaging techniques and appliances used are medical imaging tools such as, but not limited to radiography, X-ray, ultrasound or fluoroscopy for 2D images and computer tomography (CT) scans, magnetic resonance imaging (MRI) scans or ultrasound for 3D images. It is noted that from a combination of 2D images a 3D model can be constituted (e.g. according to U.S. 61/579,927 which is incorporated herein by reference). A summary of medical imaging has been described in "Fundamentals of Medical imaging", by P. Suetens, Cambridge University Press, 2002.

The term "medical imaging" as used herein refers to techniques and processes used to create images of the human or animal body (or parts thereof), typically for clinical purposes (medical procedures seeking to reveal, diagnose or examine disease) or medical science (including the study of normal anatomy and physiology).

In particular embodiments, the method described herein may further comprise providing a preoperative planning model corresponding to the envisioned surgical intervention on the first bone. Indeed, the 3D model may allow for a detailed analysis of the bone, thereby facilitating preoperational planning. The preoperative planning model can be obtained in a number of ways, including by manual design based on anatomical knowledge.

In the method described herein, a contact surface is determined or identified on the first bone, with or without cartilage or other soft tissues, which can be used to generate one or more anatomy engagement surfaces or contact points with the first bone on the device. The contact surface may be any part of the bone which is typically available during surgery for positioning the guiding instrument onto the bone.

In particular embodiments, the identification of a contact surface can be used to ensure a specific fit of the guiding instrument on the first bone. This is ensured by providing the guide with an anatomy engagement surface or anatomy contact points which are specific to the patient's contact surface (see further). Such patient specific contact surface can be identified based on the model of the bone. However, it is also envisaged that the contact points of the guide with the first bone are standard contact points. In these embodiments the methods involve determining that the contact surface is suitable for use with standard contact points. In these embodiments, a unique and stable fit can be ensured by the combination of the contact points/surfaces with the first and second bone. In certain embodiments, two or more contact surfaces may be identified on the first bone which are suitable for positioning the guide. In the methods envisaged herein, (more particularly in step (c) above), a contact surface is also identified on the second bone, with or without cartilage or other soft tissues. The contact surface may be any part of the second bone which is typically available during surgery for positioning the guiding instrument onto the bone. Preferably, the contact surface on the second bone is close to the contact surface on the first bone. The identification of the contact surface is used in the development of the guiding instrument, more particularly, for providing a further support surface (see further) on the guide, in addition to the first contact surface or contact points. In certain embodiments, the method may comprise identifying two or more contact surfaces on the second bone which are suitable for positioning the guide.

The method described herein further encompasses determining a range of motion (ROM) of the second bone relative to the first bone, in at least one degree of freedom. Indeed, the first and second bones typically are directly or indirectly linked. For example, the first and second bone may be two adjacent bones of a single joint. In general, the term "range of motion" refers to the distance (linear and/or angular) that a movable object may normally travel relative to another object while properly attached/linked to said other object. In the context of the present method, the term "range of motion" refers to a distance (linear and/or angular) that one bone may move relative to another bone, in at least one degree of freedom. In particular embodiments, this distance may correspond to the full range of motion, i.e. the maximal distance that the second bone can travel relative to the first bone, for example from a first extreme position to a second extreme position. However, the range of motion determined in the method described herein may differ from the full range of motion.

Indeed, in particular embodiments, the range of motion determined in the method described herein, is a sub-range of the full range of motion of the second bone relative to the first bone. For example, in particular embodiments, the full range of motion need not be taken into account, if it is assumed that during surgery the surgery the bones will not be moved to the extreme positions, such as extreme flexion or extreme extension (see further).

In certain embodiments, the range of motion determined in the method described herein at least in part exceeds the actual full range of motion of the second bone relative to the first bone. More particularly, in some embodiments, the range of motion determined in the method described herein may be larger than the actual full range of motion. For example, the range of motion may be estimated based on statistical values, which indicate an average range of motion of $x°$. However, it may not be precisely known for the patient under consideration, where in this $x°$ the bones in the 3D model (based on the position when the images were taken) are positioned in. Accordingly, to take into account the full range of motion and the possibility that the bones in the 3D model are in an extreme position, the range of motion may be chosen as $2x°$, more particularly $x°$ on either side of the position in the 3D model.

Accordingly, the range of motion may be chosen as a range of motion which is considered appropriate.

As described above, a range of motion is determined in at least one degree of freedom. In general, the degree of freedom (DOF) of a mechanical system such as a bone and/or a joint refers to the number of independent parameters that define its configuration. More particularly, it is the number of parameters that determine the state of a physical system. The position of a rigid body in three-dimensional space is defined by three components of translation and three components of rotation, leading to six degrees of freedom.

In most joints, the range of motion of the bones is restricted to fewer than six degrees of freedom. Moreover, the range of motion in joints is typically dominated by angular movements. For example, the carpometacarpal joints of the fingers in humans may be classified as plane joints with one degree of freedom. In particular embodiments, the range of motion refers to the distance and/or direction a joint can move between the flexed position and the extended position. In anatomy, flexion or a flexed position refers to a position that is made possible by the joint angle decreasing. The opposite is extension, or an extended position. Accordingly flexion decreases the angle between the bones at a joint, and extension increases it.

In particular embodiments, the first and second bones meet at a joint which allows movement in more than one degree of freedom. Alternatively, the first and second bones may be indirectly attached to each other via one or more other bones, thereby allowing for movement of the second bone to the first bone in more than one degree of freedom.

Accordingly, in particular embodiments, step (d) as described herein above may comprise determining a range of motion of the second bone relative to said first bone in at least two degrees of freedom. However, this is often not required. Indeed, in many cases, the movement in one or more degrees of freedom can be easily controlled intraoperatively.

Accordingly, it may not be necessary to take into account the range of motion in all degrees of freedom.

The range of motion of the second bone may depend on the forces exerted on the bone, and/or the joints(s) between the first and second bone. Accordingly, the range of motion may be determined taking into account the forces which are expected to be exerted on the bone and/or joint(s) during surgery.

In particular embodiments, the range of motion may be determined by taking images of the bones in extreme positions such as extreme flexion and extension, and optionally one or more intermediate positions. However, if it is expected that the bones will not be positioned in one or more extreme positions, no images of these one or more extreme positions are required. In certain embodiments, the range of motion may be determined by taking images of the bones in intermediate positions only. This may be done using (medical) imaging techniques as described above.

In certain embodiments, a range of motion may be calculated based on the model provided in step (a). In particular embodiments, the range of motion may be calculated based on statistical values of the range available in literature or databases. For example statistical values for the range of motion of vertebrae are provided by Amevo et al. (B Amevo, D Worth, N Bogduk, "Instantaneous axes of rotation of the typical cervical motion segments: II. optimization of technical errors", in: Clinical Biomechanics 1991, 6, 38-46).

In particular embodiments, the step of determining a range of motion of said second bone relative to said first bone (referred to as step (d) above) of the method described herein comprises determining an outer hull corresponding to the range of motion determined for the second bone. This may facilitate designing the support surface of the surgical instrument (see further). The outer hull can be considered as the (virtual) surface or contour of the minimal space needed for the second bone to go through all movements allowable according to a range of motion which is determined as described above. Accordingly, if the range of motion is restricted to one degree of freedom, the outer hull can be considered as the (virtual) surface or contour of the minimal space needed for the second bone to move from one of the two allowable movements, for example extreme flexion, to the other allowable movement, for example extreme extension.

In other words, the outer hull can be considered as the surface of a Boolean addition of a shape corresponding to the second bone, moved over its entire range of motion. Accordingly, parts of the hull correspond to the contour of the second bone in the limits of the range of motion determined as described above. As detailed above, the limits of the range of motion may correspond to the true extreme positions of the bone, but may be any other positions which are considered relevant. The rest of the hull is determined by extremities on the second bone's surface as these extremities move between the limits. In particular embodiments, only a part of the outer hull is determined. Indeed, in certain embodiments, only the part of the hull corresponding to the range of motion of the (extremities of the) contact surface determined on the second bone in step (c) is determined, as the other parts of the hull may not be particularly useful for generating the support surface of the guiding instrument. Thus, in some embodiments, step (d) may comprise determining an outer hull corresponding to the range of motion relative to said first bone of at least the contact surface on said second bone as determined in step (c).

It is noted that steps (b), (c) and (d) as described above may be performed in any order. Indeed, it can be envisaged that the contact surfaces on the first and second bone to be used in the development of the guide are selected based on the range of motion identified for the second bone and the ability to identify a first contact surface on the first bone and a second contact surface on the second bone, which can serve as a support structure taking account the relative movement of the second contact surface. In particular embodiments, step (d) is performed after steps (b) and (c) as identified above.

In step (e) of the method described herein, a surgical guide is generated, based on the data obtained and generated in steps (a) to (d) as described above. In particular embodiments, steps (a) to (d) are performed separately and the resulting data is provided such that a surgical guide can be generated. In alternative embodiments, the envisaged methods will include steps (a) to (d) recited above and will further include step (e) comprising designing or generating a surgical guide based on the data obtained in steps (a) to (d).

Generating the guiding instrument may include designing a model of a guiding instrument or an image thereof. The design of the guiding instrument may further be provided on an information carrier or can be sent to a manufacturing facility for the manufacturing of the guiding instrument or parts thereof. Thus, in particular embodiments, the methods described herein include manufacturing the guiding instrument or parts thereof. The guiding instrument generated using the methods described herein comprises one or more anatomy engagement surfaces or anatomy contact points corresponding to at least a part of the surface of the first bone.

In particular embodiments, the guiding instrument is made to be patient-specific in that it comprises one or more patient-specific anatomy engagement surfaces or anatomy contact points, matching or corresponding to at least a part of the contact surface(s) identified in step (b) as described above. More particularly, the guiding instrument may comprise one or more engagement surfaces which match the contact surface(s), and/or combinations of specifically placed anatomy contact points such as pins corresponding to specific parts of said contact surface.

However, as detailed above it is also envisaged that in particular embodiments, the anatomy engagement surface(s) or anatomy contact point(s) may be standard elements. Indeed, in some cases, patient-specific anatomy engagement surfaces and/or patient-specific anatomy contact points do not offer a sufficient added value over standard elements. This is particularly the case when the first bone is a small bone, or a bone without pronounced features, such as a vertebra or a phalanx bone. Although standard elements typically do not provide a unique fit as such, a unique fit may be provided by the combination of the standard elements and a support surface (see further).

In particular embodiments, the guiding instruments may comprise one or more anatomy engagement surfaces which are free-form structures fitting at least part of the contact surface identified in step (b). The term "free-form structure" as used herein refers to a structure having an irregular and/or asymmetrical flowing shape or contour, more particularly fitting at least part of the contour of the bone. Thus, in particular embodiments, the free-form structure is a free-form surface. A free-form surface refers to an (essentially) two-dimensional shape contained in a three-dimensional geometric space. Indeed, as will be detailed below, such a surface can be considered as essentially two-dimensional but may have a varying thickness. Typically, the free-form structure or surface is characterized by a lack of rigid radial dimensions, unlike regular surfaces such as planes, cylinders and conic surfaces. Free-form surfaces are known to the skilled person and widely used in engineering design disciplines. Typically non-uniform rational B-spline (NURBS) mathematics is used to describe the surface forms; however, there are other methods such as Gorden surfaces or Coons surfaces. The form of the free-form surfaces are characterized and defined not in terms of polynomial equations, but by their poles, degree, and number of patches (segments with spline curves). Free-form surfaces can also be defined as triangulated surfaces, where triangles are used to approximate the 3D surface. Triangulated surfaces are used in STL (Standard Triangulation Language) files that are known to a person skilled in CAD design. The free-form structures described herein are structured such that they fit the surface of the first bone specifically, thereby giving the structures their free-form characteristics.

The guide generated in step (e) of the method described herein further comprises a support surface configured for contacting at least a part of said contact surface on said second bone, over the range of motion of said second bone as determined in step (d). In preferred embodiments, the support surface matches at least a part of the outer hull as described above. More particularly, the support surface matches the part of the hull corresponding to or contributed by the contact surface determined in step (c). Consequently, when positioned on the first and second bones, the support surface will not match the entire contact surface of the second bone, but will contact the second bone only in certain locations, depending on the relative position of the adjacent bone with respect to the targeted bone. However, the support surface can contact the contact surface of the second bone, regardless of the relative position of the first and second bone. Therefore, the support surface may provide additional stability to the fit of the guide to the first bone, regardless of the relative position of the first and second bone.

In particular embodiments, the guide may comprise two or more support surfaces as described above, particularly when two or more contact surfaces are identified in step (c) as described above. Accordingly, each support surface may correspond to a part of the outer hull corresponding to or contributed by a different contact surface determined in step (c).

The guide generated using the method described herein is envisaged for use in guiding a surgical intervention on the first bone. Accordingly, the guide typically comprises at least one functional feature for guiding the surgical intervention. If the guide comprises two or more connectable elements (see further), the functional feature is typically positioned on the element having the patient-specific features for contacting the first bone.

The functional feature may be any feature which may be used for assisting and/or guiding the surgery, in any way. For example, in particular embodiments, the functional feature may comprise a clamp, which may hold another object in a specific position or orientation. In particular embodiments, the functional feature is a guiding feature selected from the list consisting of a drill guide, a screw hole, and a cutting slot. In particular embodiments, the guiding instrument can comprise one or more drill guides for guiding a screw and/or a drill. In particular embodiments, these drill guides may be removable from the guiding instrument.

In particular embodiments, the guide generated according to the method described herein further comprises one or more fixation features. This may allow for a (temporary) fixation of the guide to the first bone. In particular embodiments, this may further allow for fixation of the guide to the second bone.

However, it is envisaged that in certain embodiments, the fixation features only allow for fixation of the guide to the first bone. Indeed, fixation of the guide to the first bone constrains the relative position of the guide to the first bone.

Accordingly, after fixation, the relative position of the guide to the second bone may no longer be relevant for guiding the surgical intervention.

Fixation may be obtained via screws, wires and pins such as Kirschner wires and the like. Accordingly, in particular embodiments, the surgical guides may comprise one or more fixation features such as holes, which allow for temporary fixation of the guiding instrument onto the first (and optionally the second) bone, for example using screws, wires or pins. Thus, according to particular embodiments, the methods described herein may further comprise determining the optimal position and/or orientation of one or more fixation features for fixing the guiding instrument onto the bone and designing the guiding instrument with a fixation feature for locking onto the bone. In particular embodiments, the fixation feature is a screw hole.

The guide generated in the methods envisaged herein comprises a bridge element for connecting the anatomy engagement surface(s) (and/or anatomy contact points) and the support surface, and constraining their relative position.

In particular embodiments, the guiding instrument may be designed as a single piece comprising an anatomy engagement surface or anatomy contact points, a support surface, one or more functional features, and optionally one or more fixation features as described above. The single piece may then considered as a bridge element connecting the engagement surface (or anatomy contact points) and support surface.

In certain embodiments, the guiding instrument may comprise at least two connectable guide parts, preferably reversibly connectable parts, wherein a first guide part may comprise the anatomy engagement surface(s) (and/or anatomy contact points) as described above for positioning the guide part on the first bone, and wherein a second guide part may comprise the support surface as described above for contacting the second bone. In particular embodiments, the two guide parts may be connected directly, thereby forming a bridge connecting the anatomy engagement surface(s) (and/or anatomy contact points) for positioning the guide part on the first bone with the support surface. In other embodiments, the two guide parts may be connected indirectly via a separate bridge element.

The connection of the two or more guide parts is such that the relative position of the anatomy engagement surface(s) (and/or anatomy contact points) and the support surface is locked. Preferably, the guide parts are reversibly connectable and detachable. Indeed, once the guide is positioned correctly on the first bone, the part positioned on the first bone may be fixed to the bone, for example via fixation features as described above. After fixation, all other parts may be removed, thereby increasing the surgical window available to the surgeon.

Typically, the connection of the two or more parts may be ensured via one or more coupling features provided on each of the guide parts (and on the separate bridge element, if provided). Typically, the coupling features from the guide parts comprise pairs of matching surfaces. In particular embodiments, the coupling features may comprise pairs of matching protrusions and recesses. This helps to maintain the detachable guide parts in position during use. In particular embodiments, the coupling features may form one or more systems selected from interlocking features, a snap-fit system, a dovetail system, a pinned system and a magnetic system.

It will be appreciated by the skilled person that in certain embodiments, the guiding instrument generated by the method described herein may further comprise a support surface for contacting a third bone, preferably adjacent to the first bone. For example, the first bone may be a vertebra which is positioned in between a second and a third vertebra. Accordingly, the method described herein may further comprise the steps of:

(c') identifying a contact surface on the third bone;
(d') determining the range of motion of the third bone relative to the first bone in at least one degree of freedom.

The above description of second bone, and related elements such as the contact surface of the second bone, a range of motion of the second bone, the support surface for contacting the second bone and the like apply, mutatis mutandis, to the third bone.

In further embodiments, the guiding instrument generated by the method described herein may further comprise a support surface for contacting further bones adjacent to the first bone.

In particular embodiments, the method described herein further comprises the step of manufacturing a guiding instrument according to the design obtained in step (e) as described above (step (f)).

Manufacturing the guiding instrument envisaged in the context of the methods described herein can involve methods that allow the generation of free-form objects according to a pre-determined design. In particular embodiments, the guiding instrument is manufactured at least partially by Additive Manufacturing (AM). If the guiding instrument comprises standard elements, e.g. standard guiding features such as drill guides, these may be made via other manufacturing methods, followed by assembly of the different elements of the guiding instrument. However, it is also envisaged that the guiding instrument is manufactured entirely via AM.

Additive Manufacturing can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3-dimensional object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The guiding instruments are thus typically made of material which is compatible with additive manufacturing and which is able to provide a sufficient stiffness to the free-form structure. Suitable materials include, but are not limited to polyurethane, acrylonitrile butadiene styrene (ABS), polycarbonate (PC), PC-ABS, polyamide, polyamide with additives such as glass or metal particles, methyl methacrylate-acrylonitrile-butadiene- styrene copolymer, resorbable materials such as polymer-ceramic composites, etc. Examples of commercially available materials are: DSM Somos® series of materials 7100, 8100, 9100, 9420, 10100, 1 1 100, 121 10, 14120 and 15100 from DSM Somos; ABSplus-P430, ABSi, ABS-ESDI, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, CobaltChrome and Stainless Steel materials; Maranging Steel; Nickel Alloy; Titanium; the PA line of materials, PrimeCast and PrimePart materials and Alumide and CarbonMide from EOS GmbH.

Further provided herein is a surgical guide obtainable by the method described herein. The guiding instruments obtainable by these methods comprise one or more anatomy engagement surfaces and/or anatomy contact points for positioning the instrument on the first bone, and further comprise a support surface configured for contacting a second bone adjacent to the first bone.

More particularly, provided herein is a surgical instrument for guiding a surgical intervention on a first bone, said instrument comprising:
(1) one or more anatomy engagement surfaces or anatomy contact points corresponding to at least a part of the surface on the first bone;
(2) a support surface configured for contacting at least a part of a second bone adjacent to said first bone, over the entire range of motion of the second bone in at least one degree of freedom;
(3) a bridge element connecting the anatomy engagement surface or anatomy contact points and the support surface; and
(4) a functional feature for assisting and/or guiding the surgical intervention.

The guiding instruments obtained by the method described herein may be particularly advantageous for guiding a surgical intervention on a small bone. Indeed, small bones may not provide a sufficient surface area for allowing a stable fit of a surgical instrument on the bone. This may be remedied by the support surface as described herein. The guiding instruments obtained by the method described herein may further be advantageous for guiding a surgical intervention on a bone without pronounced features. The available contact surface on such bones may not provide a unique fit of a surgical instrument on the bone. Again, this may be remedied by the support surface configured for contacting a second bone. Further provided herein is a computer program configured for carrying out the methods for generating guiding instruments as disclosed herein. In particular embodiments, computer programs, which, when running on a computer, generate the guiding instruments as disclosed herein are provided. In particular embodiments the computer programs are adapted to perform the different steps of the methods described herein. In further embodiments, computer programs comprise software code adapted to perform the steps of the methods described herein. The data processing system or computer program particularly refer to computer aided design and manufacturing systems and programs such as CAD/CAM systems or programs. Said computer programs typically comprise tools for loading images of the bones, tools for generating a 3D model of said bones based on the images, tools for generating an outer hull based on said 3D model, tools for designing the guiding instrument, and optionally tools for instructing a manufacturing system to manufacture the guiding instrument according to the generated design.

The following examples are provided for the purpose of illustrating the present invention and by no means are meant and in no way should be interpreted to limit the scope of the present invention.

EXAMPLES

Guide for Positioning on a Vertebra

Figure 1:
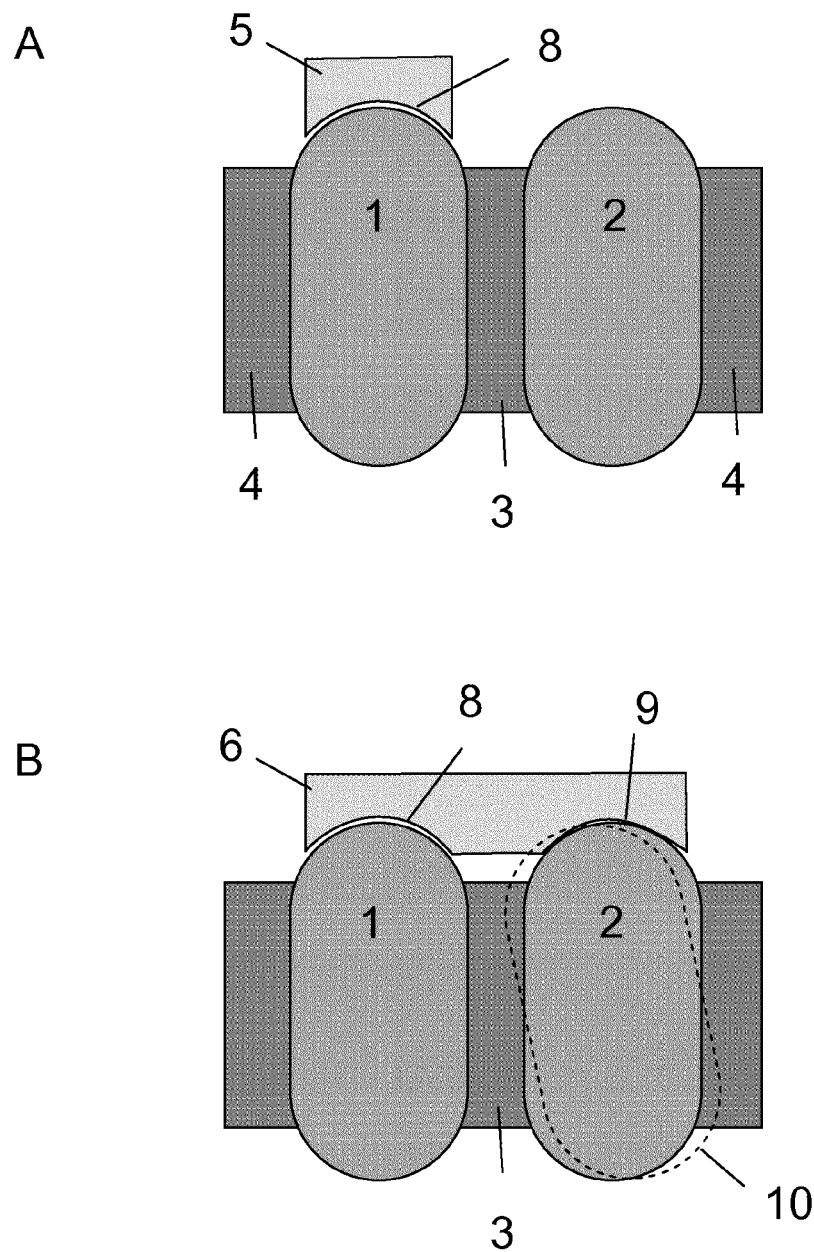
FIG. 1 A, B: schematic illustration of two adjacent vertebrae (1, 2). A: A surgical guide (5) is positioned onto a vertebra (1) via an engagement surface (8).

FIG. 1 A is a schematic illustration of two adjacent vertebrae (1, 2) joined by an intervertebral disc (3). A surgical intervention on the first vertebra (1) is envisaged. The intervention may involve operations such as drilling and cutting, for which guidance via a guiding instrument is desired.

FIG. 1 A further shows a typical guiding instrument (5) known in the art, positioned on the vertebra (1) via a patient-specific engagement surface (8) matching a part of vertebra surface. However, the surface of the vertebra available as contact surface for the surgical instrument (5) is narrow. Indeed, most of the vertebra surface area is unavailable, as it is covered by intervertebral discs (3, 4). Moreover, the available contact surface has few or no pronounced features. Consequently, the engagement surface (8) of the guiding instrument does not provide a sufficiently unique and stable fit. Accordingly, the guiding instrument cannot reliably guide the surgical intervention via its guiding features (not shown). In order to provide a sufficiently unique and stable fit, a guiding instrument (6) may be provided, comprising a first engagement surface (8) matching a part of the surface of the first vertebra (1), and a second engagement surface (9) matching a part of the surface of an adjacent vertebra (2). This is illustrated in FIG. 1 B.

By providing an engagement surface matching two vertebrae, the guiding instrument (6) provides a fit which is more stable than the fit provided by a guiding instrument (5) having only an engagement surface matching one vertebra. However, the relative position of the vertebrae (1, 2) during surgery may be different from the relative positioning of the vertebrae during the registration of medical images, which are typically used for designing the guiding instrument. Indeed, medical images are typically taken with the patient in supine position, while the surgery is performed with the patient in prone position.

A potential change of the position of vertebra (2) relative to vertebra (1) is indicated by the dotted line (10) in FIG. 1 B. In this new position, the engagement surface (9) of the guiding instrument (6) cannot be correctly positioned on both vertebrae. Correct positioning of the guiding instrument is only possible when the relative positioning of the vertebrae during surgery is identical to the relative position during the registration of medical images. In practice, this is difficult to achieve. Accordingly, the guiding instrument (6) does not reliably guide the surgical intervention via its guiding features (not shown).

A guiding instrument providing a more reliable fit may be generated using the method described herein. In this method, an available contact surface may be identified on the first and second vertebrae (1, 2), based on a 3D model of the vertebrae. For example, the surfaces contacted by the engagement surfaces (8, 9) provided on the guide (6) in FIG. 1 B may be identified as suitable contact surfaces.

A guide is then generated comprising an engagement surface matching the contact surface on the first vertebra (1). The guide further comprises a support surface for contacting the second vertebra (2). However, the support surface is designed such that the range of motion of the second vertebra (2) relative to the first vertebra (1) is taken into account.

Indeed, the method comprises the step of determining a range of motion of second vertebra (2) relative to the first vertebra (1), in at least one degree of freedom, such as rotation around an axis of rotation (11). This may be done based on statistical information available in literature or a database. The determination of a range of motion allows for determining the limits of the movement which may realistically be expected during surgery. These limits need not be identical to the extreme movements. However, in particular embodiments, the range of motion may comprise the extreme movements of the second vertebra (2) relative to the first vertebra (1). As indicated by the dotted lines in FIG. 2 A, these extreme movements typically are extreme flexion (12) and extreme extension (13).

It is noted that vertebra (2) may move relative to vertebra (1) in more than one degree of freedom. For example, in addition to rotation around the axis of rotation (11) indicated in FIG. 2, also relative rotations between the vertebrae in the axial and coronal planes are possible. However, these rotations may roughly be set to 0 by carefully positioning the patient's head during medical imaging and during surgery, and therefore need not necessarily be taken into account during the design of the surgical guide. Accordingly, the design need only take into account flexion and extension as described above, as this relative movement presents most difficulties.

Based on the knowledge of the range of motion, e.g. the extreme positions of the vertebra (2) (or any other limits of the movement of the bones considered relevant), an outer hull (14) can be determined, as shown in FIG. 2 B. Parts of the hull are contributed by the second vertebra (2) as it sits in one of the limits of the range of motion, e.g. extreme flexion (12) or extreme extension (13). The rest of the hull comes from extremities on the second vertebra's surface as the extremities move between the limits. The outer hull can be used for designing a support surface for contacting the second vertebra, thereby making the fit of the guide onto the bones more stable.

A schematic illustration of a guide (7) obtainable by the method described herein is shown in FIG. 3 A. FIG. 3 B shows the same guide, positioned on the vertebrae (1, 2).

The guide (7) comprises an engagement surface (8) for positioning the guide on the first vertebra (1), and further comprises a support surface (15) for contacting the second vertebra (2). The support surface matches the part of the outer hull (14) corresponding to the movement of the contact surface of the second vertebra.

As shown in FIG. 3 B, the support surface (15) does not match the entire contact surface of the second vertebra (2). Instead, it contacts second vertebra only in certain locations, depending on the relative position of the adjacent bone with respect to the targeted bone.

Nevertheless, the shape of the support surface allows for the guide to contact the second vertebra, regardless of the relative position of the vertebrae, and without changing the position of the guide (7) relative to the first vertebra (1).

Accordingly, the guide (7) allows for a unique and stable fit of the guide on the first vertebra. Accordingly, the guiding instrument (7) may reliably guide the surgical intervention via its guiding features (not shown).

What is claimed is:

1. A method for generating a surgical guide for guiding a surgical intervention on a first bone of a patient, the method comprising:
    (a) providing a three-dimensional (3D) model of at least a part of the first bone and of a second bone of the patient;
    (b) identifying a contact surface on the first bone;
    (c) identifying a contact surface on the second bone;
    (d) determining a range of motion of the second bone relative to the first bone in at least one degree of freedom; and
    (e) generating a surgical guide, the guide comprising:
        (1) one or more anatomy engagement surfaces or anatomy contact points corresponding to at least a part of the contact surface on the first bone;
        (2) a support surface configured to contact at least a part of the contact surface on the second bone over the entire determined range of motion of the second bone;
        (3) a bridge element configured to connect the anatomy engagement surface or anatomy contact points to the support surface; and
        (4) a functional feature for assisting the surgical intervention.

2. The method of claim 1, wherein step (d) comprises determining an outer hull corresponding to the determined range of motion relative to the first bone of the contact surface on said second bone, and wherein the support surface generated on the surgical guide matches the outer hull.

3. The method of claim 1, wherein the second bone is a bone adjacent to the first bone.

4. The method of claim 1, wherein step (d) comprises determining a range of motion of the second bone relative to the first bone in at least two degrees of freedom.

5. The method of claim 1, further comprising:
    (f) manufacturing the surgical guide via additive manufacturing.

6. The method of claim 1, wherein the first bone and the second bone are two adjacent vertebrae.

7. The method of claim 1, wherein the first bone and the second bone are adjacent phalanx bones.

8. The method of claim 1, wherein the functional feature is a guiding feature selected from the list consisting of a drill guide, a screw hole, and a cutting slot.

9. The method of claim 1, wherein the guide further comprises one or more fixation features for attachment to at least one of the first bone or the second bone.

10. The method of claim 1, wherein the guide is designed as a single piece.

11. The method of claim 1, wherein the guide is designed as two or more connectable parts.

12. The method of claim 1, wherein the bridge element is configured to connect the anatomy engagement surface or anatomy contact points at a fixed relative position to the support surface.

* * * * *